United States Patent [19]

Lee

[11] 4,334,112
[45] Jun. 8, 1982

[54] PROCESS FOR PRODUCING 2,5-DICHLORO-P-XYLENE

[75] Inventor: Young-Jin Lee, South Charleston, W. Va.

[73] Assignee: Union Carbide Corporation, Danbury, Conn.

[21] Appl. No.: 948,656

[22] Filed: Oct. 5, 1978

[51] Int. Cl.$^3$ .............................................. C07C 17/12
[52] U.S. Cl. ................................................... 570/207
[58] Field of Search ...................... 260/650 R; 570/207

[56] References Cited

U.S. PATENT DOCUMENTS 3,002,027  9/1961  Lindemann et al. ............. 260/650 R
3,035,103  5/1962  Hlynski ........................... 260/650 R
4,010,214  3/1977  Gelfand ........................... 260/650 R

OTHER PUBLICATIONS

"Chlorination of Aromatic Compounds with Metal Chlorides", Kovacik & Brace, J.A.C.S., p. 5491 et seq., Nov. 1954.

Primary Examiner—Delbert E. Gantz
Assistant Examiner—Joseph A. Boska
Attorney, Agent, or Firm—D. L. Carlson; G. L. Coon; W. R. Moran

[57] ABSTRACT

Reaction of ferric chloride with 2-chloro-p-xylene yields dichloro-p-xylene having a high ratio of 2,5-dichloro-p-xylene isomer to 2,3-dichloro-p-xylene isomer.

6 Claims, No Drawings

PROCESS FOR PRODUCING 2,5-DICHLORO-P-XYLENE

BACKGROUND OF THE INVENTION

This invention relates to the production of dichlorinated paraxylene, particularly to a process which results in the predominant production of the 2,5-dichloro-p-xylene isomer.

Various processes are known in the prior art for halogenating aromatic compounds. Generally, the known processes result in the production of a mixture of halogenated products. A number of processes are disclosed for chlorinating p-xylene. These processes produce various mixtures of mono-, di-, tri-, and in some instances tetrachlorinated products. While the product can be separated into its various components, it would be desirable to have a process for the selective production of 2,5-dichloro-p-xylene, since this product is highly useful as an intermediate in the production of pesticides.

The typical prior art known processes for producing chlorinated xylenes involve reacting xylene and chlorine in an organic solvent medium in the presence of a catalyst. U.S. Pat. No. 3,002,027 discloses a process wherein chlorine and p-xylene are reacted in glacial acetic acid as a solvent. The glacial acetic acid acts as a "chlorination stopping agent" to prevent the substitution of more than 2 chlorine atoms on the p-xylene nucleus. The reaction product consists of a mixture containing both 2,3-dichloro-p-xylene and 2,5-dichloro-p-xylene in addition to 2-chloro-p-xylene. The 2,5-dichloro-p-xylene is recovered from the crude reaction product by pouring the product into water followed by re-crystallization of the precipitate from a suitable solvent such as an organic alcohol or acetic acid. In separating the crude product, however, some of the desired 2,5-dichloro-p-xylene is lost in the oily byproduct phase.

U.S. Pat. No. 3,035,103 discloses a process wherein p-xylene is reacted with chlorine in the presence of a catalytic amount of ferric chloride to produce a mixture of 2,5-dichloro-p-xylene, 2,3-dichloro-p-xylene, 2,3,5-trichloro-p-xylene, and 2,3,5,6-tetrachloro-p-xylene. The mixture is distilled to separate the dichlorinated compounds from the tri- and tetrachlorinated compounds. The 2,5-dichloro-p-xylene must be separated from the 2,3-dichloro-p-xylene by contacting the mixture with a solvent in which only the 2,3-dichloro-p-xylene is soluble.

U.S. Pat. No. 4,010,214 discloses a process for selectively chlorinating p-xylene to produce predominanty 2,5-dichloro-p-xylene which comprises reacting chlorine and p-xylene in the presence of a catalyst system comprising halides of iron and/or antimony in conjunction with a co-catalyst which is an organic sulfur compound characterized by divalent sulfur. The crude chlorination product thus produced is said to typically contain 65 to 80 percent by weight 2,5-dichloro-p-xylene, 3 to 20 percent by weight 2,3-dichloro-p-xylene, 0 to 6 percent by weight of 2-chloro-p-xylene, 0 to 8 percent by weight 2,3,5-trichloro-p-xylene and traces of 2,3,5,6-tetrachloro-p-xylene. In the working examples of the patent, the concentrations of 2,3-dichloro-p-xylene in the crude product ranged from 11.2 to 19.1 weight percent. The 2,5-dichloro-p-xylene must be separated from 2,3-dichloro-p-xylene in a manner similar to that disclosed in U.S. Pat. No. 3,035,103.

Despite the ingenuity displayed in the prior art, a simple and direct method is still sought for the selective production of 2,5-dichloro-p-xylene of sufficiently high purity that the product is useful as an intermediate in the production of pesticides without the need for complicated separation steps.

SUMMARY OF THE INVENTION

In accordance with the teachings of this invention 2,5-dichlor-p-xylene is produced in high yield by reacting 2-chloro-p-xylene and ferric chloride. The production of undesirable byproducts, notably 2,3-dichloro-p-xylene, is minimal. The product which is produced by the process of this invention usually contains greater than 90% 2,5-dichloro-p-xylene and, in many instances, greater than 95% 2,5-dichloro-p-xylene.

In view of the comparatively higher amounts of the undesired 2,3-dichloro-p-xylene which were obtained in the prior art when chlorine gas was used as the chlorinating agent, it was quite a surprising result that 2,5-dichloro-p-xylene was obtained in consistently high purity by using ferric chloride as a chlorinating agent for 2-chloro-p-xylene. Generally, the yield of desired 2,5-dichloro-p-xylene isomer obtained by the process of this invention is sufficiently high that one can use the product as an intermediate in the production of pesticides without the need to separate the isomers.

DETAILED DESCRIPTION OF THE INVENTION

Unlike many of the known processes for producing dichlorinated xylene, the process of this invention employs monochlorinated xylene, i.e. 2-chloro-p-xylene, as a reactant, rather than xylene. The 2-chloro-p-xylene precursor can be simply produced by reacting p-xylene and chlorine gas. By stopping the reaction after about 10 to 40 percent conversion of the p-xylene to chlorinated product, one ensures that substantially all of the chlorinated product is 2-chloro-p-xylene, that is, that no significant amount of higher substituted product is formed. The unreacted p-xylene can be conveniently removed by simple distillation. The reaction temperature is not critical and typically can be anywhere from 25° C. up to about 130° C. Preferably, the reaction temperature is from about 40° C. to 70° C. The reaction can be carried out with the reactants in contact with a catalytically effective amount of a chlorination catalyst such as aluminum chloride or ferric chloride. Organic sulfur compounds characterized by the presence of divalent sulfur such as those described in U.S. Pat. No. 4,010,214 can be employed as co-catalysts, if desired.

The 2-chloro-p-xylene is reacted with anhydrous ferric chloride according to the equation:

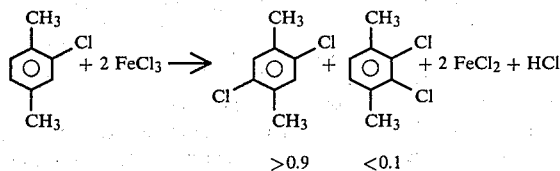

The mole ratio of 2-chloro-p-xylene to ferric chloride which is employed in the reaction is preferably at least about 1:2. While lesser amounts of 2-chloro-p-xylene can be employed, if desired, so doing may result in the production of undesirable higher chlorination products. A stoichiometric excess of 2-chloro-p-xylene can be employed, in which case the excess 2-chloro-p-xylene serves as a suitable reaction solvent. Accordingly, there is no strict upper limit on the amount of 2-chloro-p-xylene. While we prefer not to employ more than about 3 moles of 2-chloro-p-xylene per mole of ferric chloride, amounts as high as 20 moles per mole of ferric chloride could be used. Unreacted excess 2-chloro-p-xylene can be removed from the reaction mixture by simple distillation.

The temperature of reaction can vary widely and can be from about 25° C. to about 150° C. Preferably, the reaction temperature is from 60° C. to 100° C.

If desired, a chlorination catalyst such as an antimony halide or aluminum halide can be employed. Organic sulfur compounds characterized by the presence of divalent sulfur such as those described in U.S. Pat. No. 4,010,214 can be employed as co-catalysts if desired. If used, the catalysts are employed in a catalytically effective amount, typically from about 0.1 to 10 weight percent, based on the weight of 2-chloro-p-xylene. Suitable antimony halides include $SbCl_3$, $SbCl_5$, $SbOCl$, $SbBr_3$. Suitable aluminum halides include $AlCl_3$ and $AlBr_3$. Divalent sulfur compounds which can be employed as co-catalysts include dialkyl sulfides, diaryl sulfides, alkaryl sulfides, cyclic sulfides and the like. Within the preferred range of reaction temperature, I have noticed only minor increases in reaction rate as a result of using the aforementioned catalysts. At lower-than-preferred reaction temperatures, e.g. at 40° C., I have observed that use of catalysts is preferred to achieve commercially acceptable reaction rates.

The reaction need not be carried out in a solvent, however, conventional organic solvents may be used, provided they do not interfere with the reaction of the 2-chloro-p-xylene and ferric chloride. Chlorinated solvents such as methylene chloride, chloroform, ethylene dichloride, and the like, are preferred since they will not undergo chlorination by the ferric chloride. The amount of reaction solvent employed is not critical.

The reaction proceeds satisfactorily at atmospheric pressure, however, super-atmospheric or sub-atmospheric pressure can be employed if desired.

The time of reaction is not critical and can be anywhere from less than an hour to a day or more, depending on temperature, catalysis, etc. The reaction can be conveniently monitored by known means, such as gas chromatographic analysis, to determine when the reaction is complete.

In addition to the dichlorinated xylene product, the reaction generates HCl and ferrous chloride, i.e. $FeCl_2$, as byproducts. Since the HCl is a gas, it can easily be separated from the reaction mixture during the reaction. The ferrous chloride can be recovered by filtration and heated in contact with chlorine gas at a temperature from about 100° C. to 200° C. to regenerate ferric chloride. The ferric chloride can then be recycled. If the reaction is carried out in a solvent, the solvent can be removed from the product by distillation.

In view of the results of earlier reported attempts to chlorinate o- and p-xylene by reaction with ferric chloride it was quite a surprising finding that reacting ferric chloride and 2-chloro-p-xylene produced 2,5-dichloro-p-xylene in high yield and purity. Kovacic and Brace reported in 76 J.A.C.S. 5491 that reaction of ferric chloride and o-xylene or p-xylene resulted in ". . . evolution of hydrogen chloride to produce tars with no more than traces of simple chlorinated products."

The following examples are intended to further illustrate the invention described herein and not to be construed as unduly limiting the invention. Unless otherwise indicated all parts and percents are by weight.

The following procedure is typical of that used to produce the 2-chloro-p-xylene precursor of the examples. Chlorine gas was bubbled through a mixture of 42.4 grams of p-xylene, 0.1 gram phenyl sulfide, 0.1 gram aluminum chloride, and 100 ml. methylene chloride at room temperature. The reaction was carried out until about 26% of the p-xylene was converted to 2-chloro-p-xylene. Unreacted p-xylene and methylene chloride were separated from the 2-chloro-p-xylene by distillation.

EXAMPLE 1

A mixture of 28.2 g. (0.2 mole) of 2-chloro-p-xylene and 33 g. (0.2 mole) of anhydrous ferric chloride was placed in a 100-ml. flask equipped with a mechanical stirrer and a condenser having a gas bubbler at its top. This represents a 100% stoichiometric excess of 2-chloro-p-xylene which was employed as a reaction solvent. The mixture was heated at 65°–68° C. and stirred for about 7 hours, at which time gas chromatographic analysis indicated the chlorination to be complete. The reaction mixture was cooled to room temperature. The mixture was then washed three times with 50 ml. of methylene chloride. Ferrous chloride was removed by filtration. The methylene chloride containing the product was washed three times in 100 ml. of water, dried over anhydrous sodium sulfate, and concentrated by vacuum distillation to remove the solvent. The final product weighed 30.3 g. (96% yield). Gas chromatographic analysis indicated the weight ratio of 2,5-dichloro-p-xylene to 2,3-dichloro-p-xylene to be 98:2.

I have found that washing the product in water removes impurities which can cause tarry residues to form when the product is subjected to distillation.

EXAMPLE 2

Using a procedure similar to that of Example 1, 14.1 g. (0.1 mole) of 2-chloro-p-xylene was reacted with 33 g. (0.2 mole) of anhydrous ferric chloride by stirring for 24 hours at 58°–59° C. The product was purified in a manner similar to that of Example 1 to give 16.4 g. (95% yield) of final product. Gas chromatographic analysis indicated the following composition of the product.

2-chloro-p-xylene 4.4%
2,5-dichloro-p-xylene 93.2%
2,3-dichloro-p-xylene 2.1%
Unknown 0.3%

The product is suitable for use as an intermediate in the production of pesticidal compounds without further separation steps.

EXAMPLE 3

A mixture of 28.2 g. (0.2 mole) of 2-chloro-p-xylene and 65 g. (0.4 mole) of anhydrous ferric chloride was placed in a 100 ml. flask equipped with a mechanical stirrer and a condenser having a gas bubbler at its top. The mixture was heated to 130° C. and stirred for 1.5 hrs. The reaction mixture was then cooled to room temperature, washed with 100 ml. of methylene chloride, filtered to remove ferrous chloride, and concentrated by vacuum distillation to remove the methylene chloride. The product weighed 13.4 g. and had the following composition determined by gas chromatographic analysis:
2-chloro-p-xylene   5%
2,5-dichloro-p-xylene   92%
2,3-dichloro-p-xylene   3%

EXAMPLE 4

A mixture of 14.1 g. (0.1 mole) of 2-chloro-p-xylene and 33 g. (0.2 mole) of anhydrous ferric chloride was reacted in 100 ml. of refluxing ethylene dichloride at 85° C. for 18 hrs. An additional 5 g. of anhydrous ferric chloride were then added and refluxing continued for an additional 6 hrs. Gas chromatographic analysis of the crude product mixture indicated the following composition:
2-chloro-p-xylene   2%
2,5-dichloro-p-xylene   96%
2,3-dichloro-p-xylene   2%

The crude product was purified by vacuum distillation under 0.5 mm. Hg pressure to give 12.5 g. of final product.

EXAMPLE 5

To a mixture of 14.1 g. (0.1 mole) of 2-chloro-p-xylene and 35 g. (0.2 mole) of anhydrous ferric chloride in 25 ml. of methylene chloride solvent there were added, as catalysts, 0.5 g. each of diphenyl sulfide and anhydrous aluminum chloride. The methylene chloride was refluxed at about 41° C. for 16 hrs. Gas chromatographic analysis showed a small amount of unreacted 2-chloro-p-xylene remaining. An additional 1 g. of ferric chloride was added and refluxing was continued for an additional 24 hrs. The product was washed in water and the ferrous chloride removed by filtration. The product was isolated by vacuum distillation under 0.5 mm. Hg pressure to give 16.8 g. (97% yield) of final product. Gas chromatographic analysis indicated the final product composition to be as follows:
2-chloro-p-xylene   3%
2,5-dichloro-p-xylene   95%
2,3-dichloro-p-xylene   2%

EXAMPLE 6

The procedure of Example 5 was repeated with the exception that the reaction was carried out in refluxing ethylene dichloride (50 ml., reflux temperature about 85° C.). Gas chromatographic analysis indicated the final product composition to be as follows:
2-chloro-p-xylene   3%
2,5-dichloro-p-xylene   92%
2,3-dichloro-p-xylene   5%

EXAMPLE 7

A procedure similar to that of Example 5 was carried out with the exception that 0.3 g. of aluminum chloride was employed as catalyst. The reactants were heated in refluxing methylene chloride for 24 hrs. Gas chromatographic analysis indicated that the final product had the following composition:
2-chloro-p-xylene   34%
2,5-dichloro-p-xylene   64%
2,3-dichloro-p-xylene   2%

The analysis of the product indicated that, while the ratio of 2,5-dichloro-p-xylene to 2,3-dichloro-p-xylene in the product was excellent, conversion of the 2-chloro-p-xylene was incomplete after 24 hours reaction time. This is believed due to the relatively low reaction temperature in refluxing methylene chloride. At this temperature (about 41° C.), it is preferred to employ a divalent sulfur-containing co-catalyst, as was done in Example 5, to improve the yield of product.

EXAMPLE 8

A mixture of 14.1 g. (0.1 mole) of 2-chloro-p-xylene and 38.9 g. (0.24 mole) of anhydrous ferric chloride was heated in 50 ml. of refluxing methylene chloride for 5 days in the absence of any catalyst. Gas chromatographic analysis indicated that the product had the following composition:
2-chloro-p-xylene   18%
2,5-dichloro-p-xylene   81%
2,3-dichloro-p-xylene   1%

This example again illustrates the relatively low rate of conversion at the reflux temperature of methylene chloride. Note, however, the excellent ratio of 2,5- to 2,3-dichloro-p-xylene product.

EXAMPLE 9

In a manner similar to example 1, ferric chloride was reacted with a 100% stoichiometric excess of 2-chloro-p-xylene to produce 2,5-dichloro-p-xylene. Ferrous chloride which was filtered from the reaction product was heated to 120°–130° C. while in contact with chlorine gas to regenerate ferric chloride. Using a procedure similar to that of Example 1, the regenerated ferric chloride was reacted with 2-chloro-p-xylene. Gas chromatographic analysis of the purified final product indicated that the weight ratio of 2,5-dichloro-p-xylene to 2,3-dichloro-p-xylene was 96:4.

What is claimed is:

1. A process for producing dichlorinated p-xylene having a high ratio of 2,5-dichloro-p-xylene to 2,3-dichloro-p-xylene isomers which comprises reacting 2-chloro-p-xylene and anhydrous ferric chloride at a temperature of from 25° C. to 150° C.

2. A process as claimed in claim 1, wherein said reaction is carried out at a temperature of from 60° C. to 100° C.

3. A process as claimed in claim 1, wherein the molar ratio of 2-chloro-p-xylene to ferric chloride employed is from about 1:2 to 20:1.

4. A process as claimed in claim 1, wherein the molar ratio of 2-chloro-p-xylene to ferric chloride is from 1:2 to 3:1.

5. A process for producing dichlorinated p-xylene having a high ratio of 2,5-dichloro-p-xylene to 2,3-dichloro-p-xylene isomers which comprises:
   (A) heating p-xylene in contact with chlorine and a chlorination catalyst at a temperature of 25° C. to 130° C. until 10 to 40% of the p-xylene has been converted to 2-chloro-p-xylene;
   (B) separating the 2-chloro-p-xylene from the reaction product; and
   (C) reacting the 2-chloro-p-xylene thus obtained with anhydrous ferric chloride at a temperature of from 25° C. to 150° C. to obtain the desired dichlorinated p-xylene.

6. A process for producing dichlorinated p-xylene having a high ratio of 2,5-dichloro-p-xylene to 2,3-dichloro-p-xylene isomers which comprises reacting 2-chloro-p-xylene and anhydrous ferric chloride at a temperature of from 25° C. to 150° C., wherein said process produces a product having a weight ratio of 2,5-dichloro-p-xylene to 2,3-dichloro-p-xylene of at least about 9:1.

* * * * *